(12) United States Patent
Staples (10) Patent No.: US 6,212,938 B1
(45) Date of Patent: Apr. 10, 2001

(54) METHOD OF DETECTING SMELL OF A VAPOR AND PRODUCING A UNIQUE VISUAL REPRESENTATION THEREOF

(75) Inventor: Edward J. Staples, Newbury Park, CA (US)

(73) Assignee: Electronic Sensor Technology LLP, Newbury Park, CA (US)

(*) Notice: Subject to any disclaimer, the term of this patent is extended or adjusted under 35 U.S.C. 154(b) by 0 days.

(21) Appl. No.: 09/323,675

(22) Filed: Jun. 1, 1999

Related U.S. Application Data
(60) Provisional application No. 60/089,641, filed on Jun. 17, 1998.

(51) Int. Cl.[7] .......................... G01N 30/86; G01N 30/076
(52) U.S. Cl. .......................... 73/23.36; 73/23.2; 73/23.34; 73/24.06; 702/176; 345/440
(58) Field of Search .............................. 173/23.2, 24.01, 173/23.36, 23.22, 23.35, 24.06; 702/176; 345/440, 133

(56) References Cited

U.S. PATENT DOCUMENTS

| | | | |
|---|---|---|---|
| 3,811,040 | * 5/1974 | Weinfurt et al. | 702/67 |
| 5,731,998 | * 3/1998 | Lotito et al. | 395/140 |
| 5,928,609 | * 7/1999 | Gibson et al. | 73/23.34 |

OTHER PUBLICATIONS
Summary of U.S. Patent No. 4,888,295 issued 1989.

* cited by examiner

Primary Examiner—Hezron Williams
Assistant Examiner—Michael Cygan
(74) Attorney, Agent, or Firm—Gene W. Arant; Larry D. Baker (57) ABSTRACT

A process whereby the olfactory response of a gas chromatograph, equipped with a focused surface acoustic wave interferometer integrating detector is converted to a visual image for the purpose of performing pattern recognition. As volatile analytes exit a gas chromatography column a Surface Acoustic Wave Interferometer is used to monitor the condensation and re-evaporation of these analytes by periodically measuring the resonant frequency of the interferometer. A time varying output parameter is then converted to a polar display. This form of electronic nose provides a recognizable visual image of specific vapor mixtures (fragrances) containing possibly hundreds of different chemical species. Because the method provides a means of adapting and learning to recognize new vapors using these images, it is a useful method for testing chemical compositions as well as the vapors associated with bacteria and human disease.

15 Claims, 11 Drawing Sheets

| (a) ANALYSIS TIME | (b) CRYSTAL FREQUENCY (-500 MHz) | (Fig.7) CRYSTAL FREQUENCY - CONSTANT OFFSET | (Fig.8) FREQUENCY DIFFERENCES F(N)-F(N+1) |
|---|---|---|---|
| 0 | 49506.2 | 6.2 | |
| 0.023 | 49506.2 | 6.2 | 0.00 |
| 0.043 | 49529.3 | 29.3 | 23.10 |
| 0.063 | 49544.8 | 44.8 | 15.50 |
| 0.083 | 49570.6 | 70.6 | 25.80 |
| 0.103 | 49585.9 | 85.9 | 15.30 |
| 0.123 | 49608 | 108 | 22.10 |
| 0.143 | 49622.2 | 122.2 | 14.20 |
| 0.163 | 49641.9 | 141.9 | 19.70 |
| 0.183 | 49659.3 | 159.3 | 17.40 |
| 0.203 | 49669.6 | 169.6 | 10.30 |
| 0.223 | 49684.5 | 184.5 | 14.90 |
| 0.243 | 49693.1 | 193.1 | 8.60 |
| 0.263 | 49705.7 | 205.7 | 12.60 |
| 0.283 | 49719 | 219 | 13.30 |
| | | 227 | 8.00 |
| 9.843 | 50814.6 | | |
| 9.863 | 50814.6 | 1314.6 | 0.00 |
| 9.883 | 50813.7 | 1313.7 | -0.90 |
| 9.903 | 50812.9 | 1312.9 | -0.80 |
| 9.923 | 50812.7 | 1312.7 | -0.20 |
| 9.943 | 50812.9 | 1312.9 | 0.20 |
| 9.963 | 50812.5 | 1312.5 | -0.40 |
| 9.983 | 50813.2 | 1313.2 | 0.70 |
| 10.003 | 50815 | 1315 | 1.80 |

METHOD OF DETECTING SMELL OF A VAPOR AND PRODUCING A UNIQUE VISUAL REPRESENTATION THEREOF

RELATED APPLICATION

This application claims priority of my copending U.S. provisional application Ser. No. 60/089,641 filed Jun. 17, 1998.

NO COPYRIGHT LICENSE IS IMPLIED

A portion of the disclosure of this patent contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

This invention relates generally to the display of data from test and measurement equipment, and more specifically to the display of vapor images from a gas chromatograph for ease of pattern recognition.

PRIOR ART REFERENCES

1. H. T. Nagle, S. Schiffman and R. Guitierrez-Osuna, "The How and Why of Electronic Noses", IEEE Spectrum, pg. 22–33, September 1998.
2. U.S. Pat. No. 5,289,715. "Vapor Detection Apparatus and Method Using an Acoustic Interferometer", 3/1994, Staples et. al.
3. P. Keller, R. T. Kouzes, L. J. Kangas, "Three Neural Network Based Sensor System for Environmental Monitoring", Proceedings IEEE Electro94 Conference, Boston, Mass., USA, May 10–12, 1994.
4. Robert L. Grobe, "Modem Practice of Gas Chromatography", John Wiley & Sons, copyright 1985 Part 1, Chapter 2, Theory of Gas Chromatography, pp. 50–114.

BACKGROUND OF THE INVENTION

An array of dissimilar sensors simulating the human olfactory response has become known as an Electronic Nose [Ref. 1]. An Electronic Nose provides a recognizable visual image in N-dimensional space (where N equals the number of sensors) of specific vapor mixtures (fragrances) containing possibly hundreds of different chemical species. An electronic nose is designed to quantify and characterize all types of smells universally. Sensors are selected for their chemical affinities, and chemi-sorbing polymer films are commonly used for this purpose. Many sensors can be used, and a serial polling of each sensor reading produces a histogram of sensor outputs which comprises the olfactory response of the nose.

An Electronic Nose with only a few sensors results in olfactory responses which are not correlated, and multiple sensors will commonly respond to the same vapor e.g. water vapors. Because of that, it is difficult to calibrate this type of Electronic Nose with test vapors containing more than one compound. Speed and sensitivity also suffer because the vapor sample being tested by the array of individual sensors must be shared equally among all sensors in the array. Additionally there must be sufficient time, typically minutes, for the vapor to be completely absorbed in the chemical coatings.

A more common chemical analysis method of analyzing vapors is to use gas chromatography (Ref 4) to separate the vapor into its individual chemical components. Common GC systems utilize long capillary columns many meters in length, and analysis times are long but accuracy and precision are high. A recent development has been the use of directly heated short chromatography columns, cooled sample traps, and focused surface acoustic wave (SAW) interferometric vapor detectors (Ref. 2).

The SAW detector produces a variable frequency in response to analytes condensing upon and evaporating from the surface of a temperature controlled piezoelectric crystal. Unlike previous GC detectors which measure the flux of the column effluent, the SAW detector measures the total integrated amount of the vapor components as they exit the GC column and condense onto the crystal; it may therefore be referred to as an integrating detector.

Conventional chromatographic data is displayed in a rectilinear format or histogram of detector output signal versus elution time, commonly referred to as a chromatogram. The conventional chromatogram is not well suited to pattern recognition of a visual image, however.

It has been a known practice to utilize a polar display of the outputs from a sensor array. Each sensor output is then arbitrarily assigned a circumferential position in such a display. See References 1 and 3.

SUMMARY OF THE INVENTION

A new method of producing images from chromatographic data is the object of this invention. The new method of this invention involves a polar display format with a mathematical closure of the data set from which a visual image is created that is ideally suited to pattern recognition. Such images represent a visual olfactory response which is well suited to pattern recognition by humans as well as computers. Although the method is applicable to conventional GC detectors, it is best utilized with integrating SAW detectors. Two different types of polar images representing the olfactory response can be created using this new method.

In accordance with the present invention a method of detecting the smell of a vapor and producing a unique visual representation suitable for pattern recognition is described. The method is carried out using successive and rapid frequency measurements of a surface acoustic wave (SAW) integrating gas chromatography detector. First a vapor sample is collected, and second, the vapor sample is injected into the carrier gas of a gas chromatograph. In passing through the chromatography column individual analytes or chemical compounds within the vapor are separated and are detected as they exit the chromatography column. The instantaneous frequency of the SAW detector is proportional to the total amount of each compound that condenses onto or evaporates from a temperature controlled surface.

Third, two mathematical data vector sets consisting of successive (a) time and frequency measurements and (b) time and incremental frequency difference divided by incremental time, are formed. These are measurements spanning the analysis period during which chemical compounds are exiting the gas chromatography column. The two data sets represent, respectively, the condensation and the flux of condensation signature of the vapor sample.

Fourth, closed polar images are displayed by assigning the radial angle to time and the radial amplitude equal to frequency or frequency difference. The images are thus formed by transforming the time variable to a radial angle with the beginning and end of the analysis occurring at 0° or 360°. Furthermore, all adjacent data points on the display are connected by lines.

An object of the invention is therefore, to display images showing the unique characteristic of the sample vapor or fragrance in a visual form which is amenable to recognition by humans and also by pattern recognition algorithms. A polar plot of chromatogram time with the radial direction being the sensor signal or the derivative of sensor signal provides an important graphical feature well suited to Electronic Nose pattern recognition algorithms [Ref 3].

A further object of the invention is to provide a high speed process which is able to detect and analyze very small amounts of vapor and produce a distinctive image from which pattern recognition is accomplished easily by humans or computer programs.

TOTALLY SEPARATE AND APART FROM AND UNRELATED TO THE OTHER OBJECTS OF THE INVENTION SET FORTH ABOVE, it is nevertheless an object of the invention to provide a method for responding to a time-varying parameter occurring throughout a predetermined time period so as to create a closed-figure image for the purpose of pattern recognition.

DETAILED DESCRIPTION OF THE INVENTION

The GC/SAW Electronic Nose System utilizes gas chromatography apparatus in conjunction with a SAW detector, as described in my prior U.S. Pat. No. 5,289,715.

Figure 1:
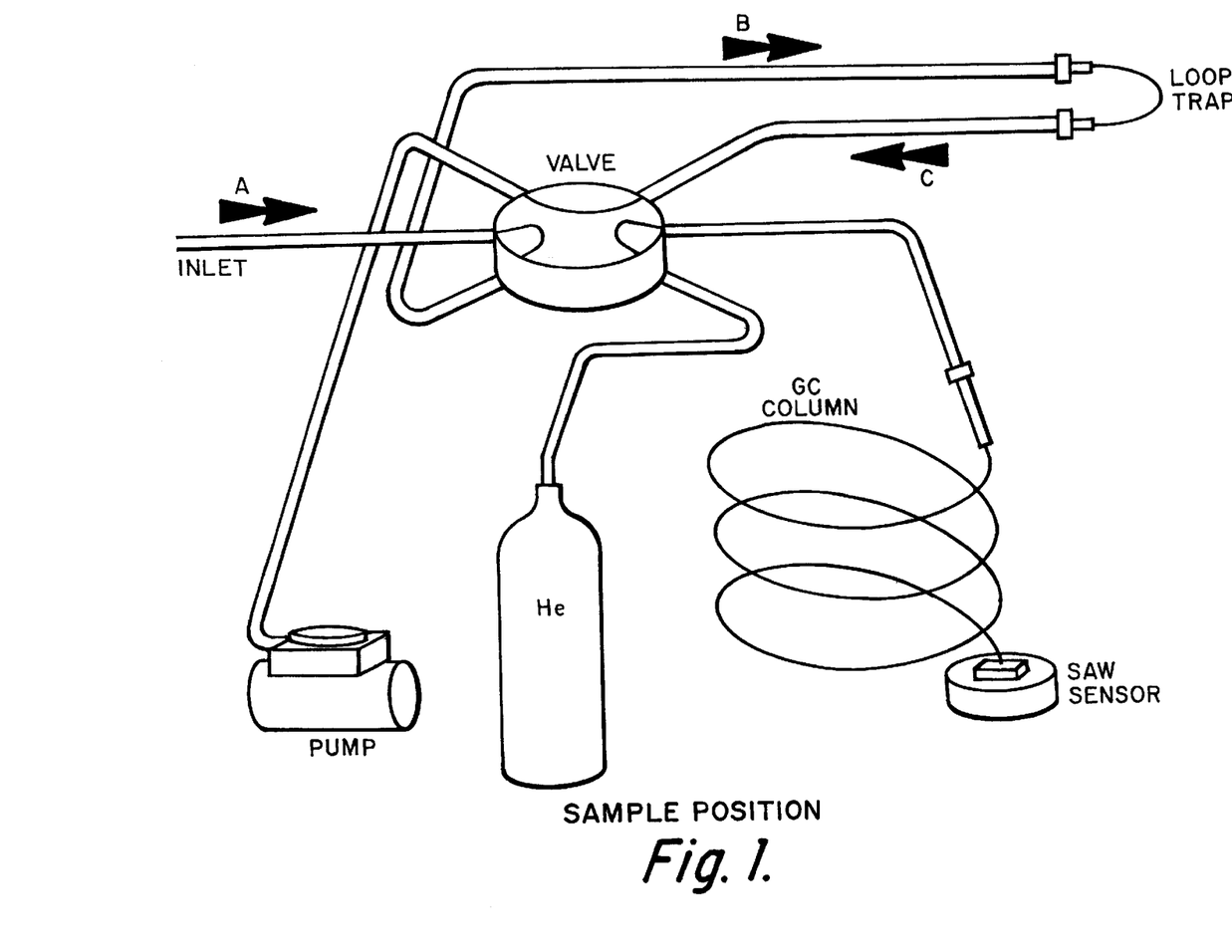
FIG. 1 is a schematic drawing of an apparatus including a SAW crystal for acquiring and storing a quantity of vapor to be tested.

Operation consists of a vapor collection cycle followed by an Injection and Analysis cycle, corresponding to the two positions of a six-port valve. During the vapor collection cycle, FIG. 1, the system collects condensable vapors from the air using an internal pump to pull ambient inlet air along path A, B, C through the sample trap. Inlet air passes through the absorbent surfaces within the trap and condensable vapors are adsorbed in the trap. By varying the collection time the Electronic Nose is able to process and analyze vapor concentrations over a wide range. Five to 10 seconds of collection time typically produces parts per billion (ppb) sensitivity for most volatile organic compounds, while only one or two seconds is required for concentrations in the high parts per million range, such as automobile exhaust.

Figure 2:
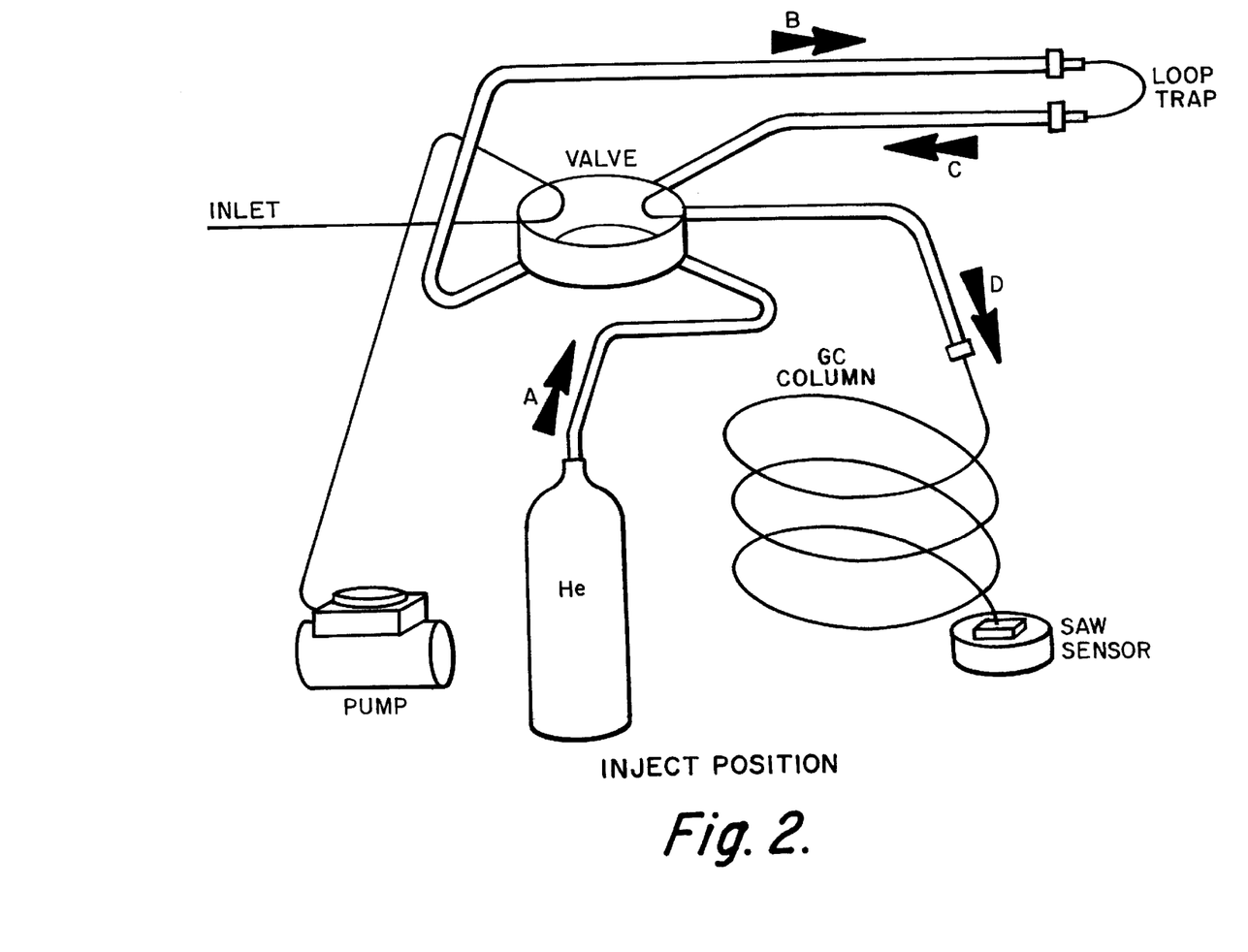
FIG. 2 shows the same apparatus when switched to the inject position and to start the analysis time period.

The Injection and Analysis cycle is initiated by moving the valve to the FIG. 2 position so that high purity helium gas flows from helium supply He through the absorbent trap section and then as indicated by arrow D into a capillary tube called a gas chromatography or GC column. Actual injection occurs when the absorbent trap is heated quickly by a short burst of electrical current, flowing for perhaps one or two milliseconds, which releases the adsorbed vapor materials that are then carried away by the helium carrier gas flow.

The adsorbed material is swept into the capillary column in a single quick burst of a few milliseconds by the helium carrier gas to start an inject-and-analysis period. The analysis period is preferably about ten seconds, but the actual input into the GC Column occurs within a very small portion of the 10-second analysis period. The He gas then transports the desorbed vapor pulse to and through the downstream chromatography column.

Figure 3A:
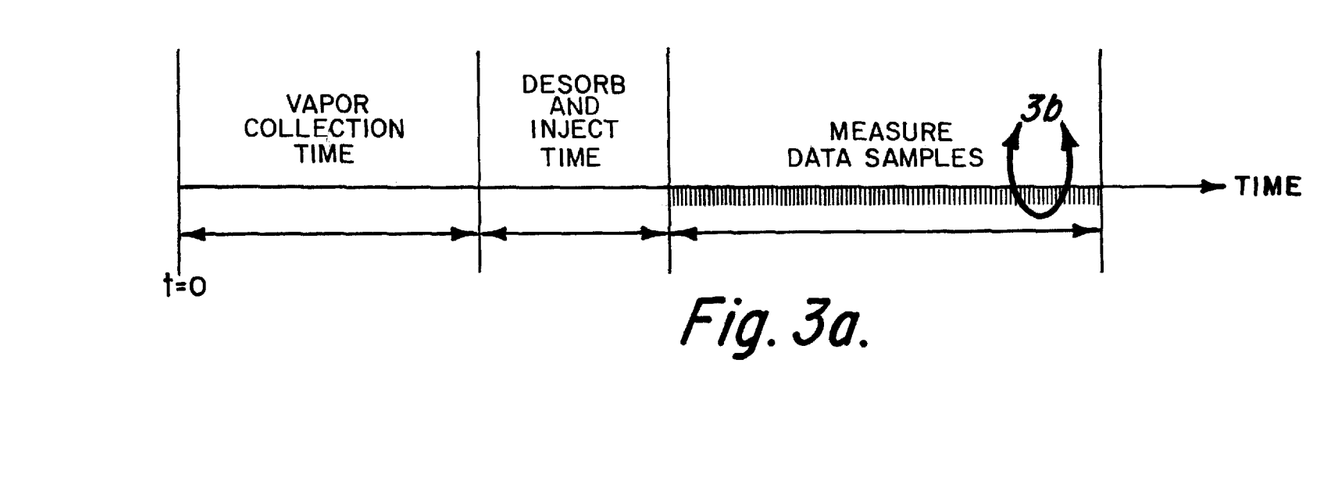
FIGS. 3(a) and 3(b) schematically illustrate the various time periods involved in the overall process.
Figure 3B:
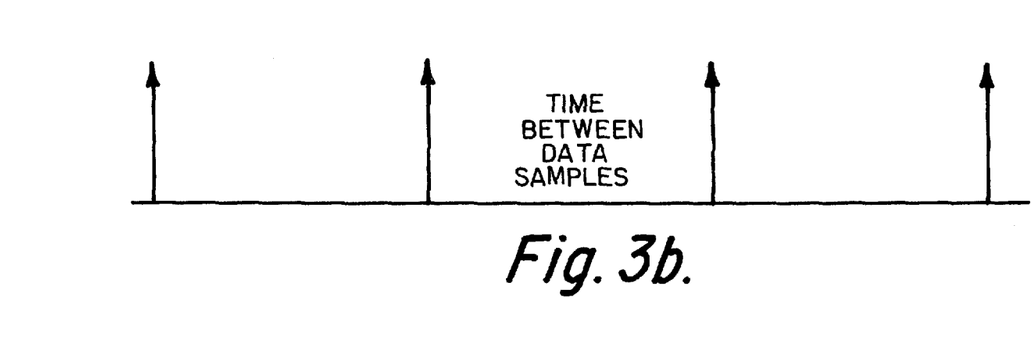

FIG. 3 indicates in a general fashion the various time periods involved in the overall process. The main purpose of FIG. 3 is to show that the time intervals between the adjacent data samples of the output signal are a very small portion of the analysis time period.

The chromatography column consists of a short section of glass or metal capillary tubing approximately 0.25 millimeters in diameter. The internal surfaces of the capillary are coated with a bonded liquid phase compound with specific chemical properties which enable the short burst of desorbed vapors to spatially separate as they pass through the column. The column temperature is closely controlled to optimize separation of the individual analytes within the vapor burst. The solubility of a compound in this liquid phase determines the time required for an analyte to travel down the Column. This characteristic time is called the Retention Time. Typical retention time for a typical GC/SAW Electronic nose is 10 seconds, however, improved resolution and peak separation can be achieved by using lower column temperatures and longer retention times.

As each analyte or compound exits the GC column it is detected by a surface acoustic wave (SAW) vapor condensation sensor. Analysis consists of monitoring the sensor signal as the materials sequentially exit the column. The SAW sensor consists of a temperature controlled quartz crystal oscillator which produces a very stable and constant frequency. As material from the column condenses on the crystal the frequency is changed in direct proportion to the amount of material received. By comparing the retention time and frequency shift with that of known vapor standards, the GC is able to quantify the composition of the original vapor sample.

Figure 4:
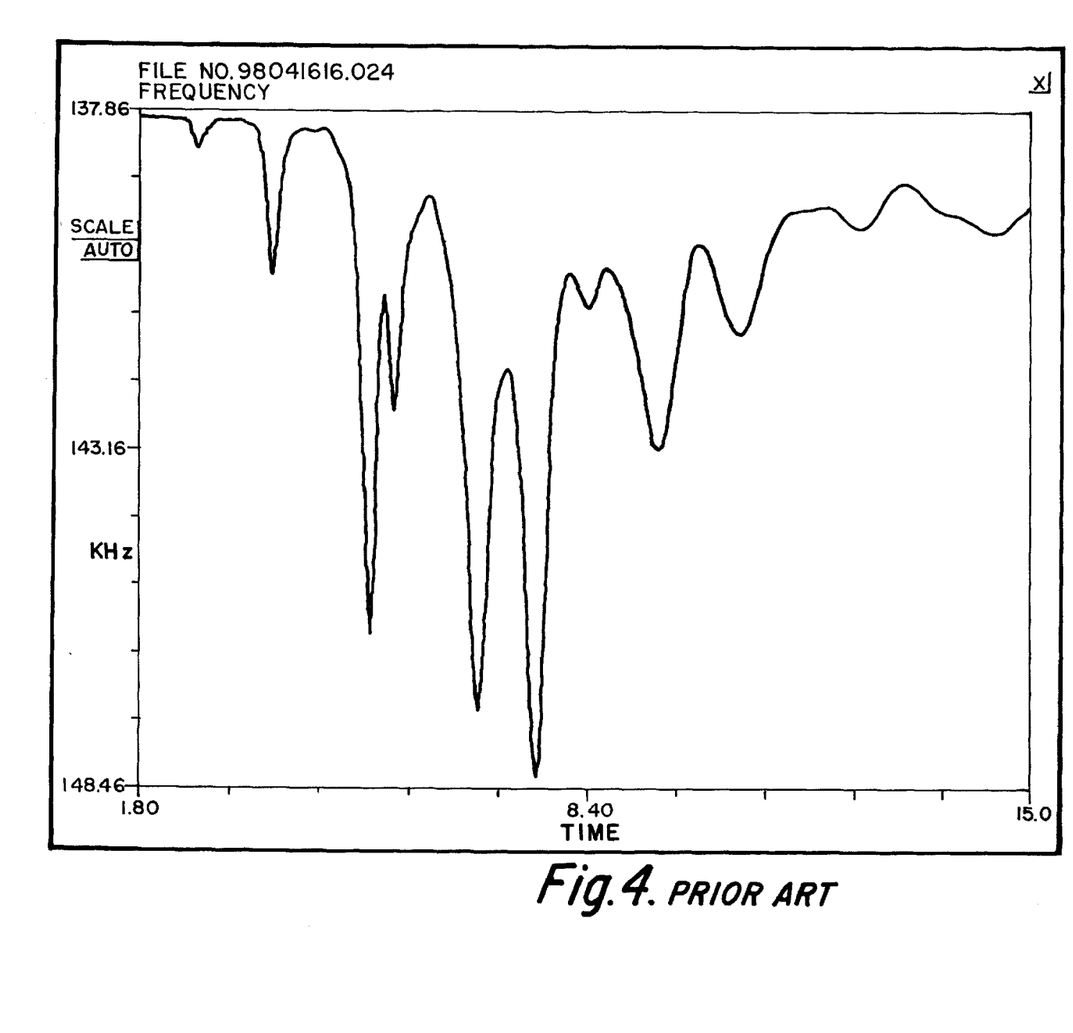
FIG. 4 shows the typical output of a SAW gas chromatograph as described in issued U.S. Pat. No. 5,289,715.
Figure 5:
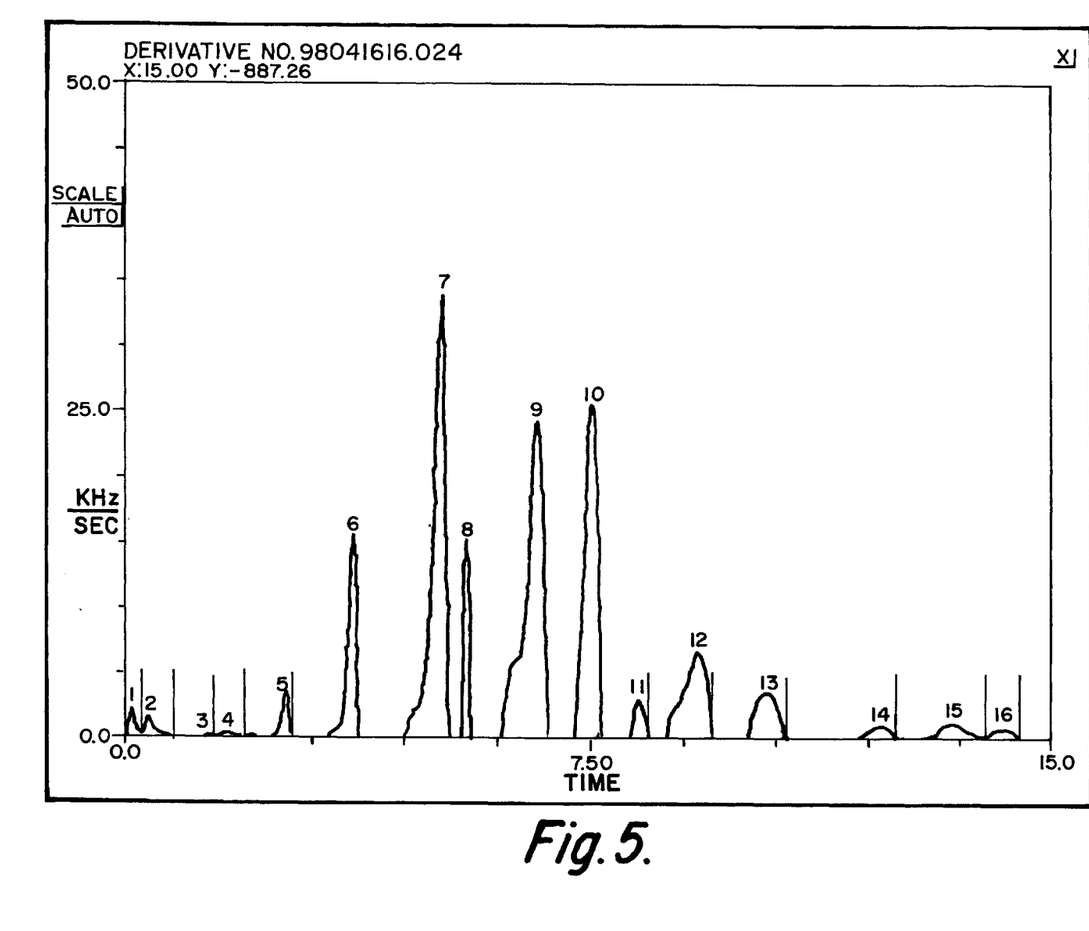
FIG. 5 shows the derivative of a typical output of a SAW gas chromatograph, illustrating different analytes which correspond to different peaks on the derivative plot.

The SAW detector produces a variable frequency in response to analytes condensing upon and evaporating from the surface of a quartz crystal. The trace in FIG. 4 displays the frequency histogram while the trace in FIG. 5 displays the derivative of frequency (Column flux) and produces the familiar peaks of chromatography. Because the SAW detector measures the integral of the chromatogram peaks, it is called an integrating detector.

MATHEMATICAL CONVERSION OF OUTPUT DATA

Figure 6:
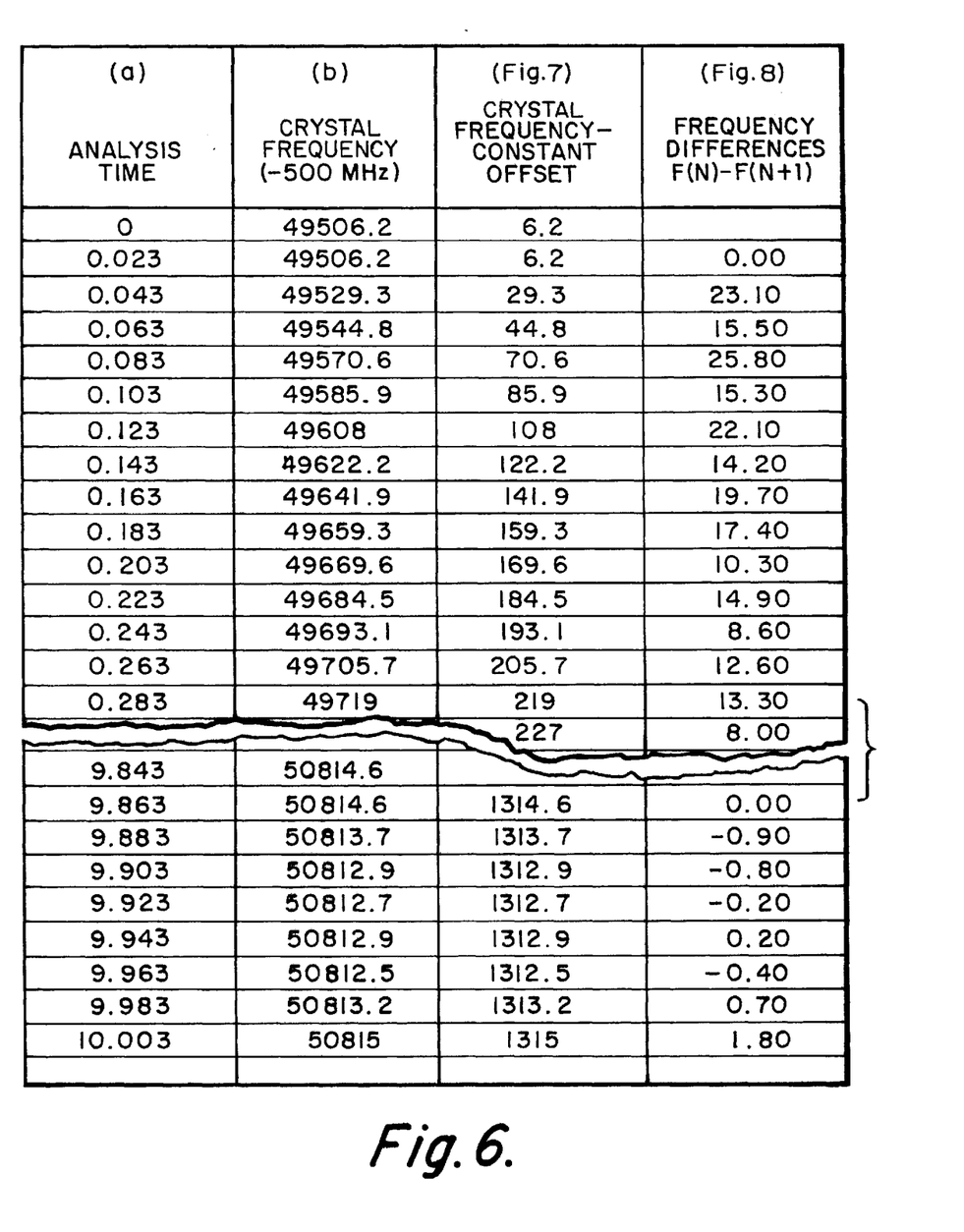
FIG. 6 is a table of frequency changes of the SAW crystal showing how frequency differences can be easily derived by a MICROSOFT EXCEL® program.

FIG. 6 is a table showing how the data for the frequency histogram may be obtained using a Microsoft-Excel® program. The frequency values in the third column of FIG. 6 are plotted as a polar display in accordance with the present invention. An image is formed by transforming the time variable to a radial angle with the beginning and end of the analysis occurring at 0° or vertical. In addition to plotting each data point at a corresponding circumferential position, line are drawn between data points to produce a closed image of the detector frequency.

Although the example of FIG. 6 shows the use of a Microsoft-Excel® program, my currently preferred implementation is a Microsoft Visual Basic® program running on a Pentium® computer, with the mathematical conversion and display routines integrated with the hardware control program.

Figure 8:
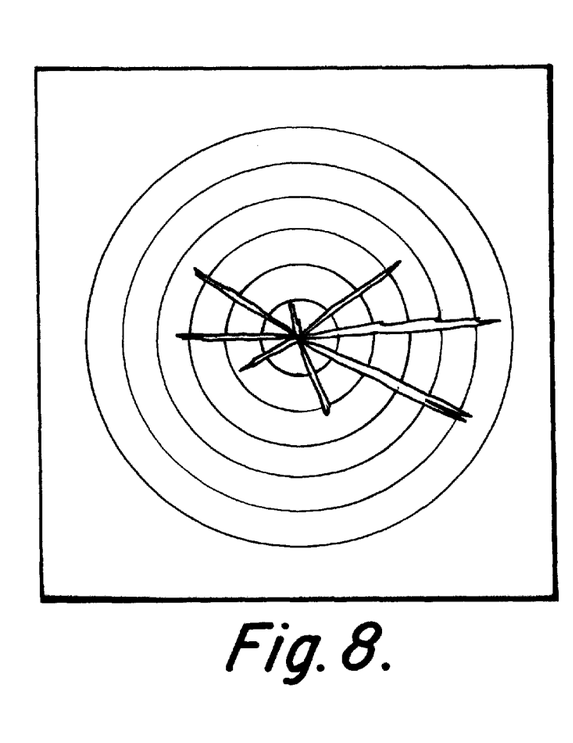
FIG. 8 is a polar diagram corresponding to the fourth column of FIG. 6.

A similar closed-image polar display is shown in FIG. 8 for the derivative of frequency, which corresponds to the fourth column of the table of FIG. 6.

According to the present invention a polar plot of a chromatogram shows time as an angular position, with the magnitude or value in the radial direction representing the sensor signal or the derivative of the sensor signal. This method of displaying the measurement results provides an important graphical feature that is well suited to being recognized by Electronic Nose pattern recognition algorithms. It also provides unique images that are easily recognizable by humans.

THE MATHEMATICAL-GRAPHIC-VISUAL METHOD

Thus the present invention provides a method of visibly displaying information that is initially available as a time-varying parameter occurring throughout a predetermined time period. The objective of the method is to create a closed-figure image for purpose of pattern recognition. The steps are as follows.

First, the time-varying parameter (in this example, the chromatography output of FIG. 4) is measured at spaced time intervals to produce a time sequence of spaced samples. I prefer to interrogate the SAW device at intervals of twenty milliseconds to determine its frequency. For an analysis time period fixed at ten second this provides a total of 500 interrogation points. The measurement information from each interrogation point is sent to the display device.

Secondly, the display device that is selected or established has a substantially circular display area with a defined center. Each sample of measurement information is then assigned to a different circumferential position within the display area, such that the sample positions are angularly separated in accordance with their original time spacings. Since I prefer to interrogate the SAW device periodically at twenty millisecond intervals, in the preferred practice of the invention this means that the measurement samples occupy 500 positions that are equally angularly spaced about the center of the display device. The 500 sample positions correspond to both the analysis time period of 10 seconds and the 360 degree circumference about the center of the display device.

Third, at each circumferential position in the display area I create a data point whose radial distance from the defined center of the display area is proportional to the value of the corresponding sample of the SAW output.

Figure 7:
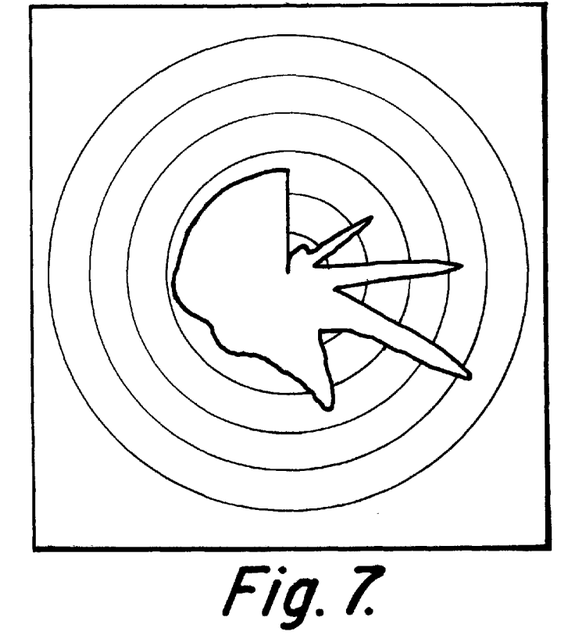
FIG. 7 is a polar diagram corresponding to the third column of FIG. 6.

Further, as a fourth and very important step, in addition to displaying the data points themselves I also draw a line between each two adjacent data points, including the first and last data points. This interconnection of the data points creates a closed-figure image as shown in FIG. 7.

The display shown in FIG. 8 is constructed in the same manner, but using the frequency difference values of the fourth column of FIG. 6.

ALTERNATE FORMS

While a tabular method of data analysis and display has been described using the well-known Microsoft Excel® program to create the example, it will be evident to those persons skilled in the art that appropriate computer programs can be constructed to control the periodic interrogation of the SAW output and the placement of the resulting data points on the display device.

The SAW sensor detects the amount of analyte condensing upon (and evaporating from) a quartz surface, and the SAW frequency corresponds to the total (integral) amount of analyte condensed. The SAW crystal is believed to be the only integrating GC detector; all others detect the flux of column effluent flow. The derivative of the detector output is only used to determine retention time. The amount of analyte detected is determined by sensor frequency.

Figure 9:
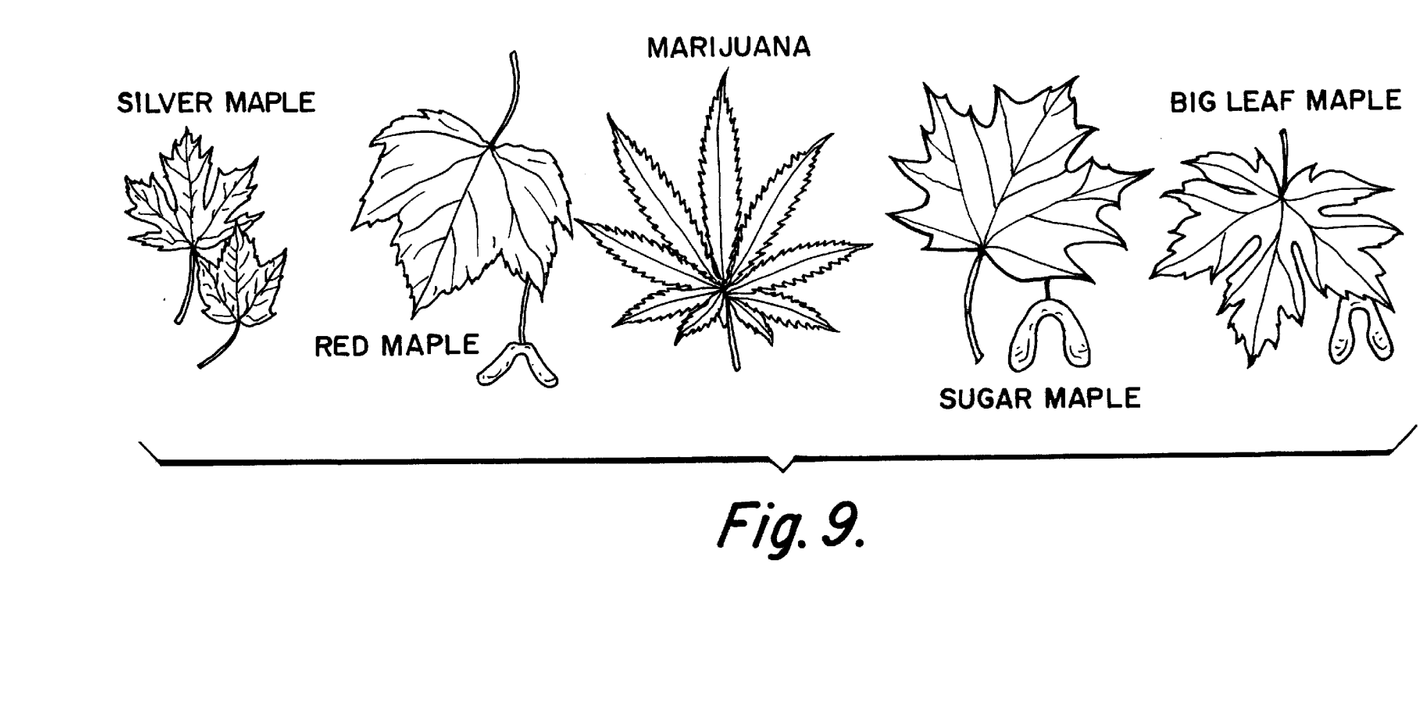
FIG. 9 is an illustration of the different visual images of the leaves of well known trees and plants.

Several electronic nose pattern recognition algorithms based upon sliding sets of correlations using known compound patterns associated with complex fragrances were evaluated. The objective was to find the best "pattern recognition algorithm". Thus far nothing approaching the performance of a human operator has been found. The situation is demonstrated in the pictures of plant leafs shown in FIG. 9. For a human, identification of the marijuana leaf is simple and immediate, while for computation algorithms the task can be daunting, long, and tedious. For a similar reason screeners at airport security checkpoints remain as trained humans.

Figure 10A:
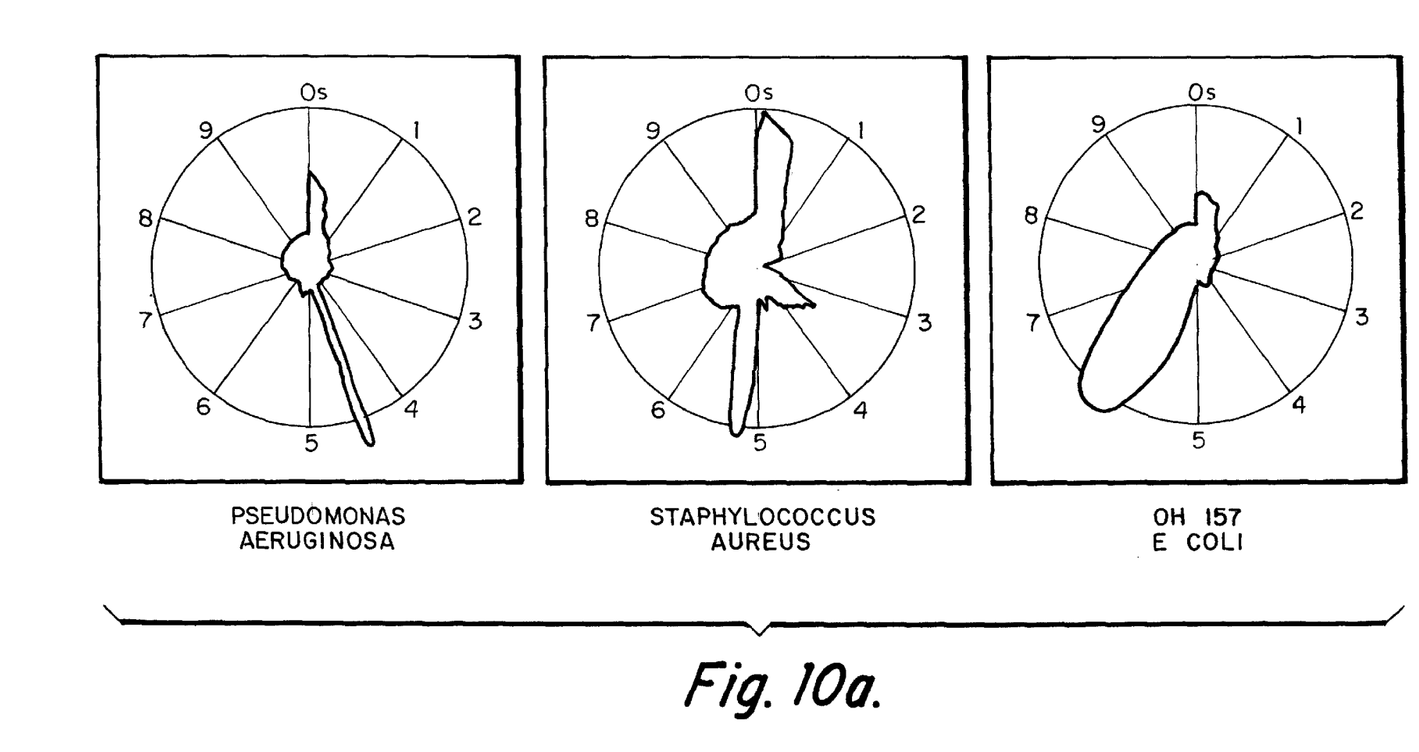
FIG. 10 is a group of chromatrographs that respectively represent the smells of different vapors or substances, as produced in accordance with the method of the present invention.
Figure 10B:
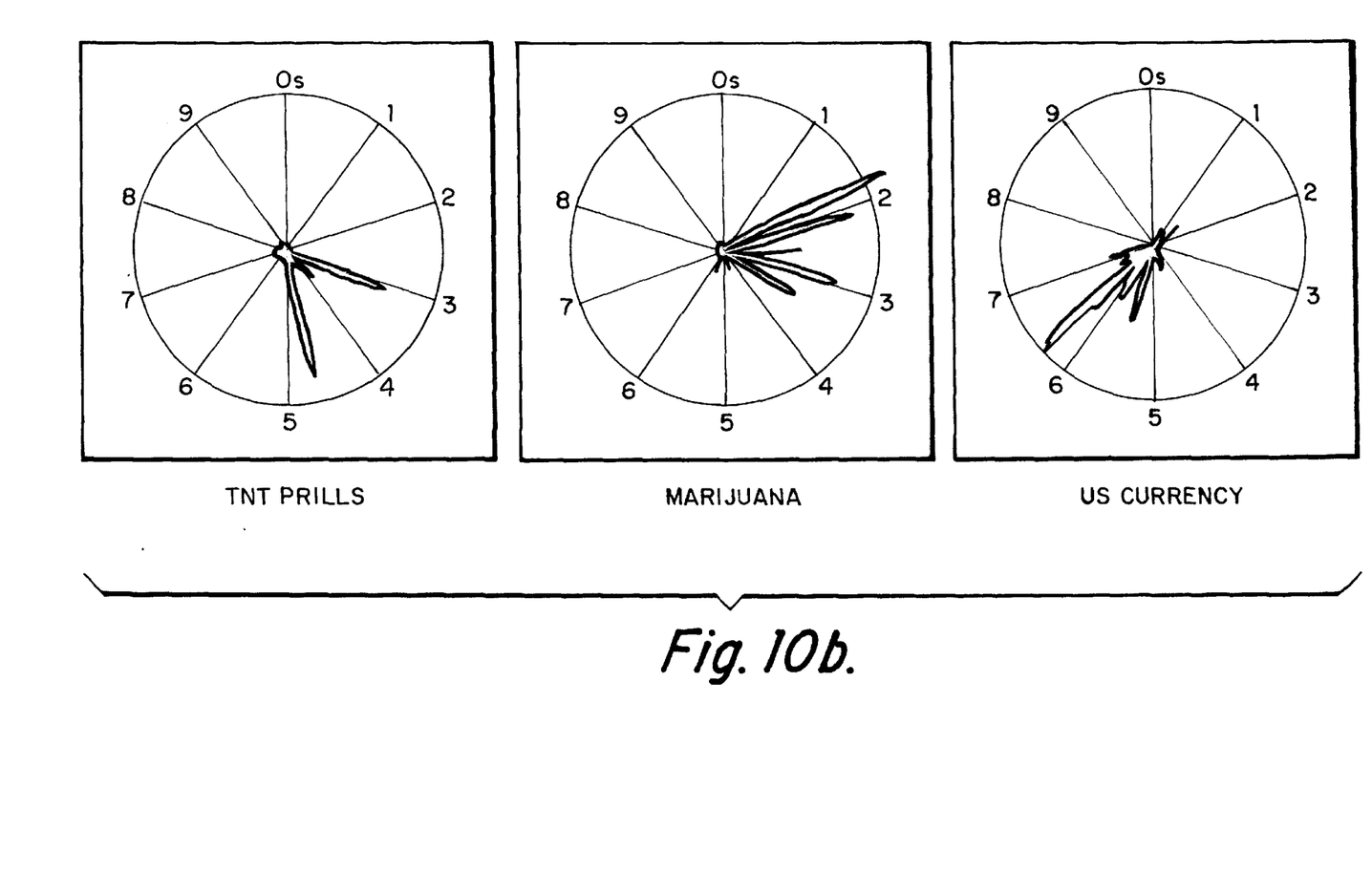
Figure 10C:
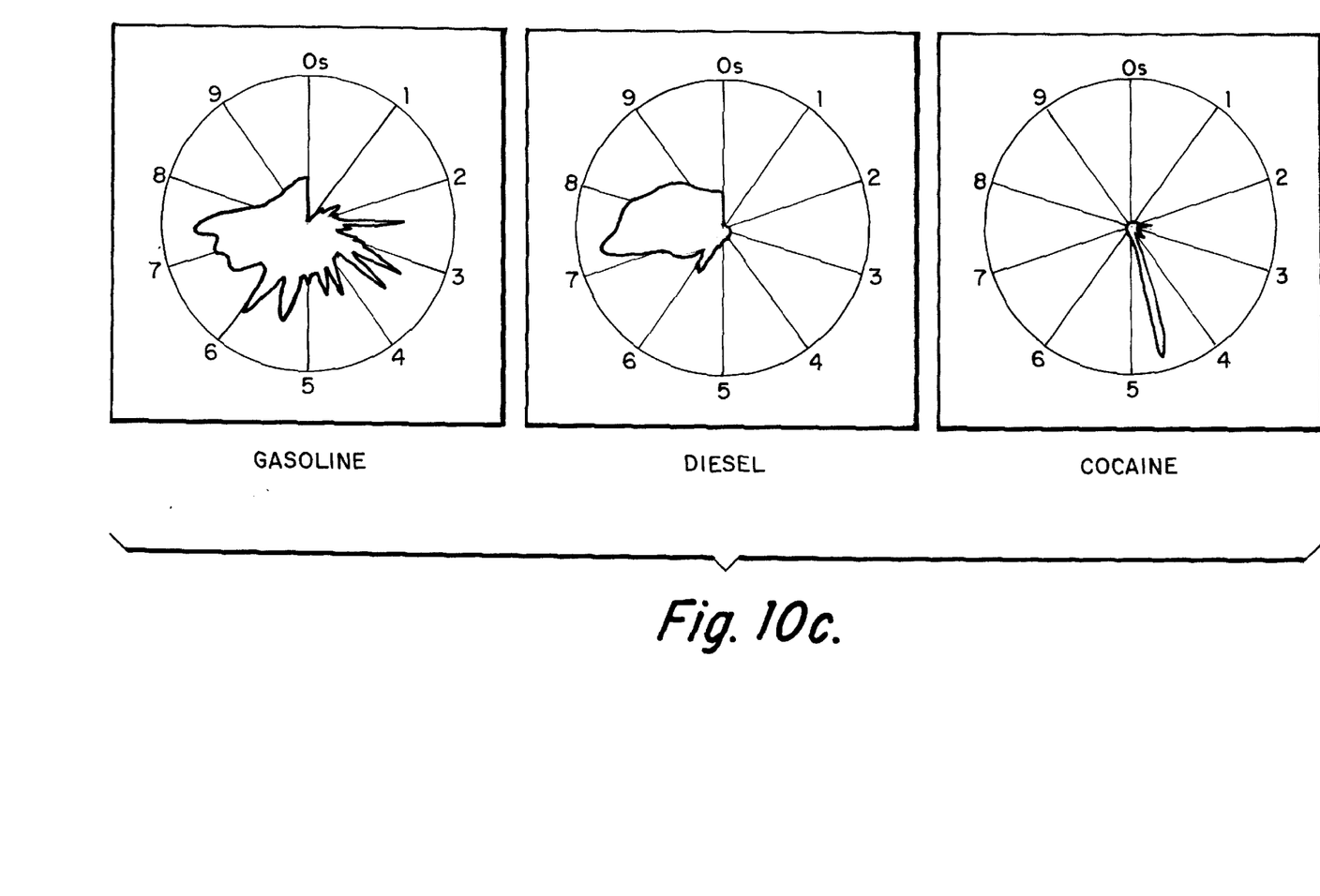

Humans must be trained to recognize image patterns; however, they excel when properly trained with visual olfactory images. Some example images from infectious bacteria, drugs of abuse, and flammable fuels created in accordance with the present invention are shown in FIG. 10. From experience in conducting numerous tests utilizing the method of the present invention is has been shown that human operators are able to recognize certain images or food smells because they looked like common shapes.

Thus the Electronic Nose operating in accordance with the novel method of the present invention provides a recognizable visual image of specific vapor mixtures (fragrances) containing possibly hundreds of different chemical species. This Electronic Nose has the ability to recognize as well as quantify many different and sometimes complex fragrances. That result is achieved using pattern recognition and a visual fragrance pattern, derived from an integrating solid-state detector., the SAW device. A graphic image allows a complex ambient environment to be viewed and recognized as part of a previously learned image set. Using the ability of a law enforcement officer, for example, to recognize visual patterns will allow quick assessment of smells or vapor that could not otherwise be detected within permissible time limits.

What I claim is:

1. In the art of gas chromatography, a method of detecting a vapor that contains a plurality of chemical analytes, and providing a visual representation of its odor characteristics that can be uniquely and readily identified by humans, comprising the steps of:

a. supplying a carrier gas having a collection of the vapor desorbed therein to a gas chromatographic column so as to separate the vapor's chemical analytes in time;

b. during a predetermined analysis period, applying the effluent vapor from the chromatographic column to a SAW device that includes a vibratory crystal having a base frequency, such that different analytes exit the chromatography column at different times to physically interact with the surface of the crystal;

c. also during the analysis period, repetitively interrogating the SAW device to measure the vibration frequency of the crystal;

d. applying signals representing the deviations of the measured crystal frequencies from the base frequency to a display device to produce a polar representation in which a complete rotation corresponds to the difference in time between the beginning and ending of the analysis period, such that the data points on the display device are separated by angles proportional to the time differences between data points; and e. adding lines on the display interconnecting adjacent data points, thereby producing a unique closed-image visual pattern which is distinctly indicative of the odor of the vapor.

2. The method of claim 1 wherein the SAW device is interrogated periodically.

3. The method of claim 1 wherein the SAW device is interrogated periodically at twenty millisecond intervals.

4. The method of claim 1 including the additional step of creating an additional polar representation that displays a mathematical derivative of the first-named polar representation, indicative of the flux of the column effluent.

5. The method of claim 3 including the additional step of creating an additional polar representation that displays a mathematical derivative of the first-named representation, indicative of the flux of the column effluent.

6. In the art of gas chromatography, a method of detecting the smell of an odor that contains a plurality of chemical analytes, and providing a visual representation of its odor characteristics that can be uniquely and readily identified by humans, comprising the steps of:

a. supplying a carrier gas vehicle having a collection of the vapor desorbed therein to a gas chromatographic column so as to separate the chemical vapor analytes in time as they exit the chromatography column.;

b. during a predetermined analysis period, applying the effluent vapor from the chromatographic column to a physical device that is capable of changing one of its physical characteristics so as to detect and quantify the amounts of material exiting the chromatography column;

c. also during the analysis period, repetitively interrogating the physical device to observe the changes occurring in that characteristic; and d. then applying signals representing the observed changes occurring in that physical characteristic to a display device to produce a polar representation in which a complete rotation corresponds to the difference in time between the beginning and ending of the analysis period, such that the data points on the display device are separated by angles proportional to the time differences between data points; thereby producing a closed-image visual pattern which is distinctly indicative of the odor of the vapor.

7. The method of claim 6 wherein the physical device is interrogated periodically.

8. The method of claim 6 wherein the physical device is interrogated periodically at twenty millisecond intervals.

9. The method of claim 6 including the additional step of creating an additional polar representation that displays a mathematical derivative of the first-named polar representation, indicative of the flux of the column effluent.

10. A method of claim 8 including the additional step of creating an additional polar representation that displays a mathematical derivative of the first-named polar representation, indicative of the flux of the column effluent.

11. A method of visibly displaying information that is received as a time-varying parameter occurring throughout a predetermined time period, so as to create a closed-figure image for the purpose of pattern recognition, comprising the steps of:

a. measuring the parameter at spaced time intervals to produce a time sequence of spaced samples;

b. establishing a substantially circular display area, having a defined center, within which to display the information;

c. allocating each sample to a different circumferential position within the display area such that the sample positions are angularly separated in accordance with their respective time spacings and the 360 degree circumference of the display area conforms precisely to the predetermined time period;

d. for each corresponding different circumferential position in the display area, creating a data point whose radial distance from the center of the display area is proportional to the value of the corresponding sample; and e. then visibly displaying not only the data points themselves, but also lines that interconnect adjacent data points, including interconnecting the first and last data points, so as to create the closed-figure image.

12. The method of claim 11 wherein the time-varying parameter is measured at equally spaced time intervals to produce a time sequence of equally spaced samples, and all of the sample positions are equally angularly spaced within the display area.

13. The method of claim 11 wherein the display area is circular.

14. The method of claim 12 wherein the display area is circular.

15. The method of claim 11 wherein a gas chromatograph is utilized to produce the time-varying parameter.

\* \* \* \* \*